(12) United States Patent
Yang

(10) Patent No.: US 10,588,520 B2
(45) Date of Patent: Mar. 17, 2020

(54) SPHYGMOMANOMETER CUFF, SPHYGMOMANOMETER WITH THE SAME AND METHOD FOR USING THE SAME

(71) Applicant: Sheng Zhou Yang, Shenzhen (CN)

(72) Inventor: Sheng Zhou Yang, Shenzhen (CN)

( * ) Notice: Subject to any disclaimer, the term of this patent is extended or adjusted under 35 U.S.C. 154(b) by 28 days.

(21) Appl. No.: 15/104,526

(22) PCT Filed: Jan. 4, 2016

(86) PCT No.: PCT/CN2016/070011
§ 371 (c)(1),
(2) Date: Jun. 15, 2016

(87) PCT Pub. No.: WO2017/059650
PCT Pub. Date: Apr. 13, 2017

(65) Prior Publication Data
US 2018/0199835 A1 Jul. 19, 2018

(30) Foreign Application Priority Data

Oct. 10, 2015 (CN) .......................... 2015 1 0652056

(51) Int. Cl.
*A61B 5/022* (2006.01)
*A61B 5/021* (2006.01)

(52) U.S. Cl.
CPC ...... *A61B 5/02233* (2013.01); *A61B 5/02141* (2013.01)

(58) Field of Classification Search
CPC .. A61B 5/02233; A61B 5/02141; A61B 5/022
See application file for complete search history.

(56) References Cited

U.S. PATENT DOCUMENTS

| | | | | |
|---|---|---|---|---|
| 2004/0186385 | A1* | 9/2004 | Mochizuki | A61B 5/02141 600/499 |
| 2006/0058688 | A1* | 3/2006 | Kishimoto | A61B 5/02233 600/499 |
| 2012/0240377 | A1* | 9/2012 | Ashida | A61B 5/02233 29/428 |
| 2016/0287104 | A1* | 10/2016 | Tsunoda | A61B 5/02233 |
| 2018/0177414 | A1* | 6/2018 | Tokko | A61B 5/022 |

* cited by examiner

*Primary Examiner* — Jacqueline Cheng
*Assistant Examiner* — Tho Q Tran
(74) *Attorney, Agent, or Firm* — John Alumit

(57) ABSTRACT

A sphygmomanometer cuff for a wearable sphygmomanometer includes a cuff body for wrapping around a predetermined portion of a body. The cuff body includes an air bag, a retaining plate, and an air tube. The air bag includes a top layer, a bottom layer, and an intermediate layer disposed between and spacing apart the top layer and the bottom layer. A sealed cavity is defined between the top layer and the bottom layer. The intermediate layer has a rough surface. The retaining plate is attached to an outer surface of the top layer of the air bag. The air tube extends through the retaining plate and connects with the sealed cavity of the air bag.

14 Claims, 4 Drawing Sheets

SPHYGMOMANOMETER CUFF, SPHYGMOMANOMETER WITH THE SAME AND METHOD FOR USING THE SAME

FIELD OF THE INVENTION

The present disclosure relates to a sphygmomanometer cuff, and more particularly to a sphygmomanometer cuff, a sphygmomanometer with the same, and a method for using the same.

BACKGROUND OF THE INVENTION

People have paid more and more attention to their health as living standards rise. More and more families deploy a variety of home medical equipments to facilitate simple health management of their family members. Blood pressure measuring device, or sphygmomanometer, has become a necessary health monitoring equipment in people's daily lives. With the development of science and technology, sphygmomanometers have become increasingly more compact, portable, and sensitive.

Nowadays, many types of portable intelligent sphygmomanometer have been developed, such as wearable sphygmomanometers for the upper arm or the wrist. These types of sphygmomanometers require cuffs (or bands) to be wrapped and fastened around the upper arm or wrist for measuring blood pressure. The cuff is typically built-in with a fluid bag for pressing arteries at certain portions of the body, such as the upper arm or the wrist. Arterial pressure wave can be detected when air is pumped into and out of the fluid bag by a built-in pump motor, so that blood pressure can be measured. Generally, the cuff includes an air bag for accommodating air and a sleeve for wrapping the air bag around the body. When wrapped around the upper arm or the wrist of a user, the cuff is also called an arm band or wrist band.

In the prior art, air bags are usually of a flat one-piece sealed rubber structure. The upper and lower rubber layers of the air bag tend to adhere to each other, therefore lowering the speed of inflation and deflation of the air bag and detection efficiency of the sphygmomanometer. In addition, poor air permeability of the rubber layers reduces the comfort of measurements.

SUMMARY OF THE INVENTION

To provide a solution to the aforementioned problems, an embodiment of the present invention provides a sphygmomanometer cuff for a wearable sphygmomanometer. The sphygmomanometer cuff includes a cuff body for wrapping around a predetermined portion of a body. The cuff body includes an air bag, a retaining plate and an air tube. The air bag includes a top layer, a bottom layer, and an intermediate layer disposed between and spacing apart the top layer and the bottom layer. A sealed cavity is defined between the top layer and the bottom layer. The intermediate layer has a rough surface. The retaining plate is attached to an outer surface of the top layer of the air bag. The air tube extends through the retaining plate and connects with the sealed cavity of the air bag.

Another embodiment of the present invention provides a wearable sphygmomanometer. The wearable sphygmomanometer includes a sphygmomanometer main body and a sphygmomanometer cuff. The sphygmomanometer cuff includes a cuff body for wrapping around a predetermined portion of a body. The cuff body includes an air bag, a retaining plate and an air tube. The air bag includes a top layer, a bottom layer, and an intermediate layer disposed between and spacing apart the top layer and the bottom layer. A sealed cavity is defined between the top layer and the bottom layer. The intermediate layer has a rough surface. The retaining plate is attached to an outer surface of the top layer of the air bag. The air tube extends through the retaining plate and connects with the sealed cavity of the air bag.

Yet another embodiment of the present invention provides a method for using a wearable sphygmomanometer. The method includes providing a wearable sphygmomanometer, and wrapping a sphygmomanometer cuff around a predetermined portion of a body. The wearable sphygmomanometer includes a sphygmomanometer main body and the sphygmomanometer cuff. The sphygmomanometer cuff includes a cuff body for wrapping around the predetermined portion of the body. The cuff body includes an air bag, a retaining plate and an air tube. The air bag includes a top layer, a bottom layer, and an intermediate layer disposed between and spacing apart the top layer and the bottom layer. A sealed cavity is defined between the top layer and the bottom layer. The intermediate layer has a rough surface. The retaining plate is attached to an outer surface of the top layer of the air bag. The air tube extends through the retaining plate and connects with the sealed cavity of the air bag. When a user wears the wearable sphygmomanometer, the air bag of the sphygmomanometer cuff abuts against the predetermined portion of the body, the top layer and the bottom layer of the air bag are disposed adjacent to each other, and the rough surface of the intermediate layer of the air bag allows a plurality of gaps to form at a contact area between the cuff body and the predetermined portion of the body. When the wearable sphygmomanometer performs a measurement of blood pressure, external air flows through the air tube to inflate the sealed cavity of the air bag, and the rough surface of the intermediate layer prevents the top layer and the bottom layer from adhering to each other. When the wearable sphygmomanometer completes the measurement, air in the sealed cavity of the air bag is released through the air tube, and the rough surface of the intermediate layer prevents the top layer and the bottom layer from adhering to each other.

According to the aforementioned embodiments, the sphygmomanometer cuff, the sphygmomanometer using the same, and the method for using the same have the following advantages:

The fabric intermediate layer disposed between the top layer and the bottom layer of the air bag can prevent adhesion between the top layer and bottom layer and thus facilitate inflation and deflation. The intermediate layer also allows the gaps to form between the sphygmomanometer cuff and the arm when the sphygmomanometer cuff is wrapped around the arm of the user, so that skin respiration and thus comfort of blood pressure measurement is enhanced.

Furthermore, the arcuate bottom surface of the retaining plate allows the air channel to form between the top layer and the bottom layer of the air bag when the sphygmomanometer cuff is wrapped around the arm of the user. The air channel facilitates inflation and deflation of the air bag and improves and measurement precision. The arcuate bottom surface of the retaining plate also allows formation of the ventable gap between the bottom surface and the arm when the sphygmomanometer cuff is fastened around the arm, so that skin respiration and comfort of measurement are enhanced.

Moreover, the protrusions intermittently formed on the bottom of the retaining plate allow the air passages to form between the protrusions and the top layer of the air bag when the sphygmomanometer cuff is inflated around the arm of the user. The air passages significantly improve the speed of inflation and deflation of the air bag. Comfort of the measurement is also enhanced.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION OF PREFERRED EMBODIMENTS

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
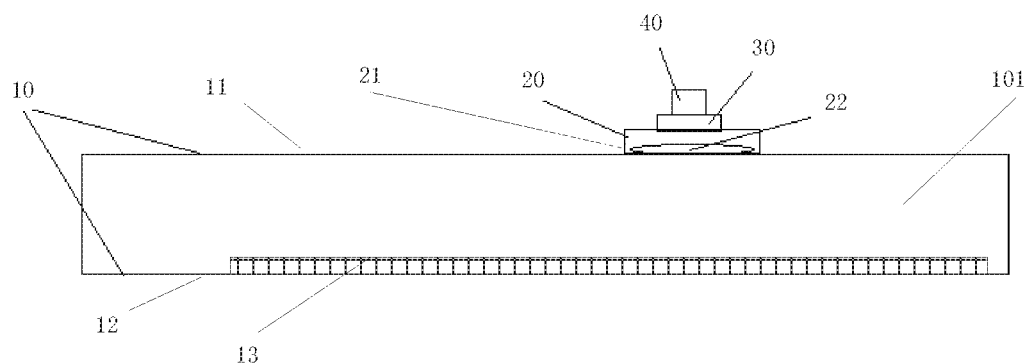
FIG. 1 is a front view of a sphygmomanometer cuff according to one embodiment of the present invention.
Figure 2:
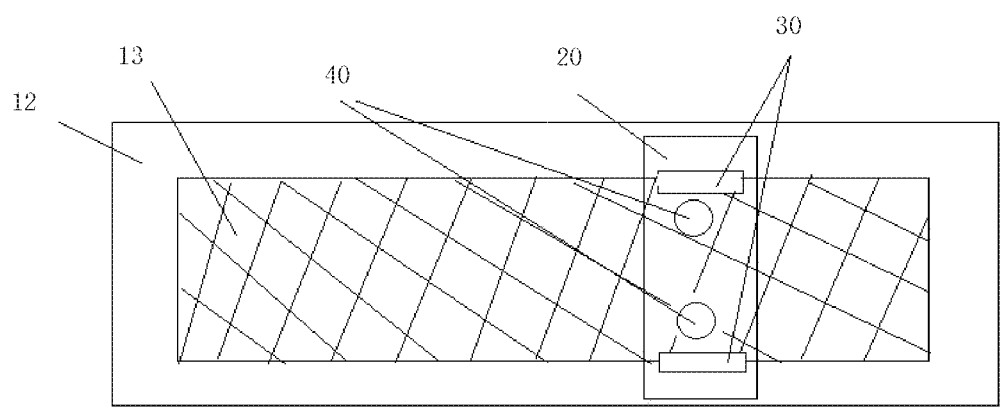
FIG. 2 is a bottom view of the sphygmomanometer cuff of FIG. 1.

Referring to FIG. 1 and FIG. 2. In this embodiment, a sphygmomanometer cuff for arm blood pressure measurement includes a cuff body for wrapping around an upper arm or a wrist of a user. The cuff body includes an air bag 10, a retaining plate 20 for securing a sphygmomanometer (not shown) to the cuff body, a fastener 30, and an air tube 40. The fastener 30 is configured to fasten the sphygmomanometer to the retaining plate 20. The air tube 40 extends through the retaining plate 20 and may secure the retaining plate 20 to the air bag 10.

The sphygmomanometer cuff may further include a self-locking ring and a molding paster. The self-locking ring and the molding paster may be disposed on two opposite sides of the cuff body for fastening the sphygmomanometer cuff to the arm of the user.

The air bag 10 may be laid flat, and includes a top layer 11 and a bottom layer 12. Edges of the top layer 11 and the bottom layer 12 are adhered to form a sealed cavity 101 defined therebetween. An intermediate layer 13 is disposed between the top layer 11 and the bottom layer 12, and spaces apart the top layer 11 and the bottom layer 12. The intermediate member 13 may be made of net fabrics with rough surfaces. A thickness of the intermediate layer 13 may range from about 0.2 millimeters to about 2 millimeters. The intermediate layer 13 may be attached to the bottom layer 12 or the top layer 11; alternatively, the intermediate layer 13, the top layer 11 and the bottom layer 12 may have a substantially identical surface area so that edges of the three layers may be overlapped and adhered. It is to be understood that the present invention is not limited thereto as long as the intermediate layer 13 separates the bottom layer 12 or the top layer 11.

The sphygmomanometer cuff may include two or more air tubes 40. Two air tubes 40 are employed in the present embodiment. The air tubes 40 extend through the retaining plate 20 and connect with the sealed cavity 101 of the air bag 10, so that air can enter the seal cavity 101 during blood pressure measurement and leave the seal cavity 101 after measurement completes.

When the sphygmomanometer begins to measure blood pressure and the air bag 10 starts to inflate, as the top layer 11 and the bottom layer 12 are spaced apart by the intermediate layer 13, the top layer 11 and the bottom layer 12 separate quickly so that air fills the air bag 10 quickly. If no intermediate layer 13 is disposed in the air bag 10, the top layer 11 and the bottom layer 12 tend to adhere to each other, and sufficient airflow is required to break the adhesion. Thus, inflation speed of the air bag 10 and measurement speed would be reduced without adopting the intermediate layer 13.

When the measurement is completed, the air in the sealed cavity 101 begins to release. During the deflation process, as the intermediate layer 13 prevents the top layer 11 and the bottom layer 12 from adhering to each other, the air in all areas of the sealed cavity 101 can be released quickly through the air tube 40, thus increasing the speed of deflation and enhancing the comfort of measurement.

When measuring blood pressure with the sphygmomanometer cuff of the wearable sphygmomanometer, the sphygmomanometer cuff is wrapped around the arm of the user and the air bag 10 abuts against the arm. The rough surface of the intermediate layer 13 allows a plurality of gaps to form at the contact area between the sphygmomanometer cuff and the arm, therefore facilitating skin respiration. In the present embodiment, the intermediate layer 13 is attached to and integrated with an inner surface of the bottom layer 12. When the air bag 10 is inflated, the top layer 11 and the bottom layer 12 are separated, the bottom layer 12 of the air bag 10 would press against the arm of the user, and the plurality of gaps are formed between the sphygmomanometer cuff and the arm. Therefore, skin of the arm may respire and comfort of the measurement is enhanced.

The retaining plate 20 may be a rectangular sheet, with a length of the retaining plate 20 slightly smaller than a width of the sphygmomanometer cuff. A longitudinal direction of the retaining plate 20 is substantially parallel to a width direction of the sphygmomanometer cuff. The retaining plate 20 includes an arcuate bottom surface 21, or for example, a half-hole disposed on the bottom surface 21 along the longitudinal direction of the retaining plate 20. The arcuate bottom surface 21 recesses toward a top surface of the retaining plate 20. Therefore, when an outer edge of the retaining plate 20 is attached to an outer surface of the top layer 11 of the air bag 10, a ventable gap 22 is formed between the bottom surface 21 of the retaining plate 20 and the outer surface of the top layer 11 of the air bag 10.

Figure 3:
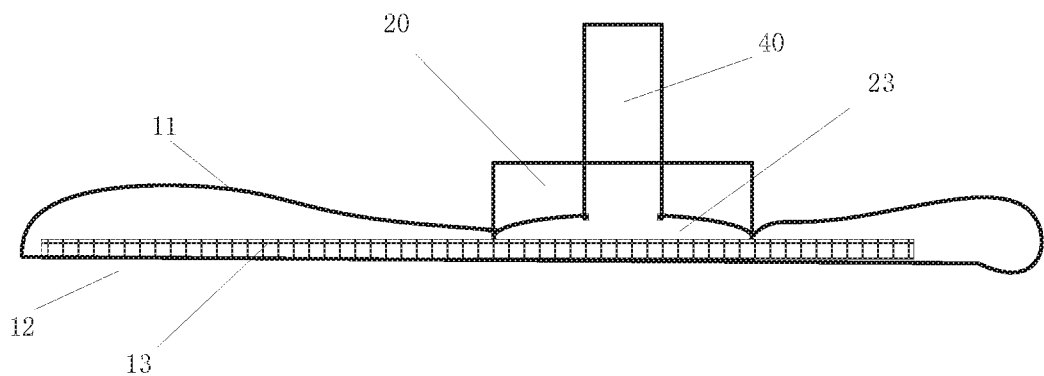
FIG. 3 is a front view of the sphygmomanometer cuff of FIG. 1 when worn by a user, showing the retaining plate with an arcuate bottom surface abutting against the air bag to form an air channel in the sealed cavity of the air bag.

Referring to FIG. 3. When the sphygmomanometer cuff is wrapped around the arm of the user, the retaining plate 20 abuts against the air bag 10, and the top layer 11 and the bottom layer 12 are disposed adjacent to each other. The arcuate bottom surface of the retaining plate 20 allows an air channel 23 to form between the top layer 11 and the bottom layer 12. The air channel 23 is connected with the air tube 40. When the measurement is completed, the air in the air bag 10 may be released through the air channel 23, thus significantly increasing the speed of deflation. Likewise, when performing blood pressure measurement, external air flow through the air tube 40 and the air channel 23 to inflate the air bag 10, thus increasing the speed of inflation. The arcuate configuration at the bottom surface 21 of the retaining plate 20 effectively enhances the speed and precision of blood pressure measurement. Meanwhile, when the sphygmomanometer cuff is fastened around the arm, the ventable gap 22 formed between the arcuate bottom surface 21 and the arm facilitates skin respiration and enhances comfort of measurement.

Figure 4:
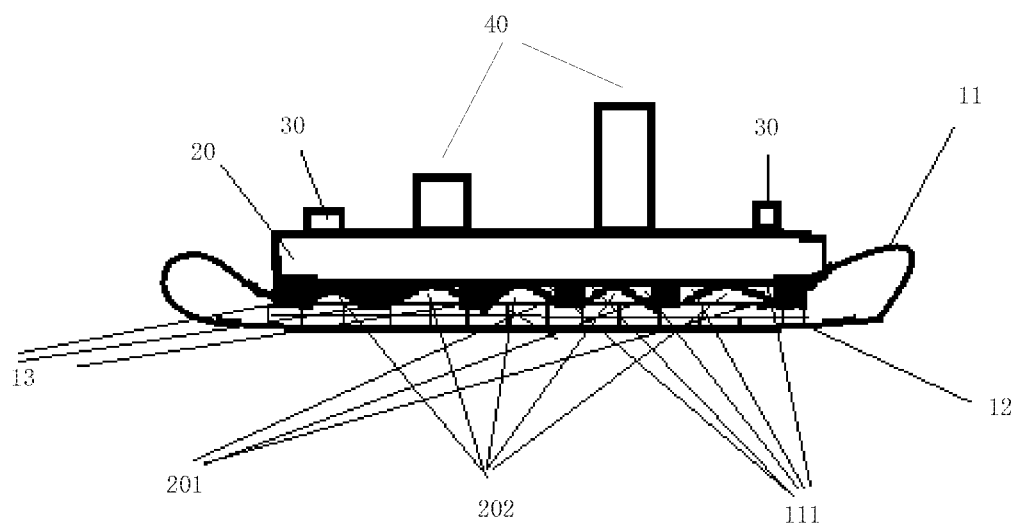
FIG. 4 is a front view of the sphygmomanometer cuff of FIG. 1 when worn by a user, showing the retaining plate with a plurality of intermittently arranged protrusions abutting against the air bag to form a plurality of intermittent air passages in the sealed cavity of the air bag.

Referring to FIG. 4. A plurality of first protrusions 201 (for example, a plurality of tiny posts) are formed intermittently on a bottom of the retaining plate 20, and contact the outer surface of the top layer 11 of the air bag 10. A plurality of interspaces 111 are formed between any two of the first protrusions 201 at the bottom of the retaining plate 20 and the outer surface of the top layer 11. Similarly, a plurality of second protrusions may also be formed intermittently on the bottom of the retaining plate 20 and surround the air tube 40. The second protrusions may have similar configuration to the first protrusions. The plurality of second protrusions contact the outer surface of the top layer 11 of the air bag 10. A plurality of interspaces are also formed between any two of the second protrusions at the bottom of the retaining plate 20 and the outer surface of the top layer 11.

When measuring blood pressure, the sphygmomanometer cuff is wrapped around the arm of the user, the retaining plate 20 abuts against the air bag 10, and the plurality of protrusions 201 contact the outer surface of the top layer 11. When the air bag 10 is inflated, the protrusions 201 press against the top layer 11, and portions of the top layer 11, the bottom layer 12, and the intermediate layer 13 corresponding to the protrusions 201 are compressed together in the air bag 10. The plurality of ventable interspaces 111 formed between the protrusions 201 depressurize the top layer 11, the bottom layer 12, and the intermediate layer 13, and internal pressure of the air bag 10 allows a plurality of air passages 202 to form at the ventable interspaces 111. As the plurality of air passages 202 are connected to the air tube 40, fast inflation and deflation of the air bag 10 is achieved.

When the measurement is completed, the air in the air bag 10 may be released through the plurality of air passages 202, thus increasing the speed of deflation. Likewise, when measuring blood pressure, the air passages 202 forms in the sealed cavity 101 during inflation, thus facilitating external air entry and enhance the speed of inflation. Comfort of the measurement is also improved.

In at least one embodiment of the present invention, a wearable sphygmomanometer is provided. The wearable sphygmomanometer includes a sphygmomanometer main body and a sphygmomanometer cuff. The fastener 30 secures the sphygmomanometer main body to the upper surface of the retaining plate 20.

In another embodiment of the present invention, a method for using the wearable sphygmomanometer according to the aforementioned embodiments is provided. The method includes the following steps:

First, providing the wearable sphygmomanometer cuff; and

Second, wrapping the sphygmomanometer cuff around the arm of the user.

In the present embodiment, when the user wears the wearable sphygmomanometer around the arm, the air bag 10 of the sphygmomanometer cuff abuts against the arm and the top layer 11 and the bottom layer 12 of the air bag 10 are disposed adjacent to each other. The rough surface of the intermediate layer 13 allows the plurality of gaps to form at the contact area between the sphygmomanometer cuff and the arm so as to improve skin respiration.

When the wearable sphygmomanometer performs blood pressure measurement, external air flows through the air tube 40 to inflate the sealed cavity 101 of the air bag 10. The rough surface of the intermediate layer 13 prevents the top layer 11 and the bottom layer 12 from adhering to each other, so as to expedite inflation of the sealed cavity 101 of the air bag 10.

When the measurement is completed, the air in the sealed cavity 101 is released through the air tube 40. The rough surface of the intermediate layer 13 prevents the top layer 11 and the bottom layer 12 from adhering to each other, so as to expedite deflation of the sealed cavity 101 of the air bag 10.

In a preferred embodiment of the present invention, the retaining plate 20 includes the arcuate bottom surface 21, and the bottom surface 21 recesses toward the top surface of the retaining plate 20. When the sphygmomanometer cuff is wrapped around the arm of the user, the retaining plate 20 abuts against the air bag 10, and the top layer 11 and the bottom layer 12 are disposed adjacent to each other. The arcuate bottom surface of the retaining plate 20 allows an air channel 23 to form between the top layer 11 and the bottom layer 12. The air channel 23 is connected with the air tube 40 for facilitating inflation and deflation of the air bag 10.

In another preferred embodiment of the present invention, the plurality of first protrusions 201 are formed intermittently on the bottom of the retaining plate 20, so that the first protrusions 201 intermittently contact the outer surface of the top layer 11 of the air bag. Similarly, in yet another preferred embodiment, the plurality of second protrusions may also be formed intermittently on the bottom of the retaining plate 20 and surround the air tube 40, so that the second protrusions intermittently contact the outer surface of the top layer 11 of the air bag 10. When the sphygmomanometer cuff is wrapped around the arm of the user, the retaining plate 20 abuts against the air bag 10, and the plurality of ventable interspaces 111 formed between the protrusions 201 allows the plurality of air passages 202 to form in the sealed cavity 101 when the air bag 10 is inflated. The air passages 202 are connected with the air tube 40, so that inflation and deflation of the air bag 10 is facilitated.

According to the aforementioned embodiments, the sphygmomanometer cuff, the sphygmomanometer using the same, and the method for using the same have the following advantages:

The fabric intermediate layer disposed between the top layer and the bottom layer of the air bag can prevent adhesion between the top layer and bottom layer and thus facilitate inflation and deflation. The intermediate layer also allows the gaps to form between the sphygmomanometer cuff and the arm when the sphygmomanometer cuff is wrapped around the arm of the user, so that skin respiration and thus comfort of blood pressure measurement is enhanced.

Furthermore, the arcuate bottom surface of the retaining plate allows the air channel to form between the top layer and the bottom layer of the air bag when the sphygmomanometer cuff is wrapped around the arm of the user. The air channel facilitates inflation and deflation of the air bag and improves and measurement precision. The arcuate bottom surface of the retaining plate also allows formation of the ventable gap between the bottom surface and the arm when the sphygmomanometer cuff is fastened around the arm, so that skin respiration and comfort of measurement are enhanced.

Moreover, the protrusions intermittently formed on the bottom of the retaining plate allow the air passages to form between the protrusions and the top layer of the air bag when the sphygmomanometer cuff is inflated around the arm of the user. The air passages significantly improve the speed of inflation and deflation of the air bag. Comfort of the measurement is also enhanced.

It is also to be understood, however, that even though numerous characteristics and advantages have been set forth in the foregoing description of the embodiments, together with details of the structures and functions of the embodiments, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. A sphygmomanometer cuff for a wearable sphygmomanometer comprising a cuff body for wrapping around a predetermined portion of a body, the cuff body comprising:
    an air bag, comprising a top layer, a bottom layer, and an intermediate layer disposed between and spacing apart the top layer and the bottom layer, a sealed cavity being defined between the top layer and the bottom layer, and the intermediate layer having an uneven surface sufficient for a plurality of gaps to form at a contact surface between the sphygmomanometer cuff and an arm of a user, and wherein the surface areas of all three layers are substantially identical so that their edges overlap each other and be adhered to each other;
    a retaining plate, attached to an outer surface of the top layer of the air bag; and
    an air tube, extending through the retaining plate and connecting with the sealed cavity of the air bag.

2. The sphygmomanometer cuff of claim 1, wherein the intermediate layer is attached to an inner surface of the bottom layer or to an inner surface of the top layer.

3. The sphygmomanometer cuff of claim 1, wherein a bottom surface of the retaining plate is arcuate, and the bottom surface recesses toward a top surface of the retaining plate.

4. The sphygmomanometer cuff of claim 1, wherein a plurality of first protrusions are formed intermittently on a bottom of the retaining plate, so that the plurality of first protrusions intermittently contact the outer surface of the top layer of the air bag.

5. The sphygmomanometer cuff of claim 1, wherein a plurality of second protrusions are formed intermittently on a bottom of the retaining plate and surround the air tube, and the plurality of second protrusions intermittently contact the outer surface of the top layer of the air bag.

6. A wearable sphygmomanometer, comprising:
    a sphygmomanometer main body; and
    a sphygmomanometer cuff, comprising a cuff body for wrapping around a predetermined portion of a body, the cuff body comprising:
    an air bag, comprising a top layer, a bottom layer, and an intermediate layer disposed between and spacing apart the top layer and the bottom layer, a sealed cavity being defined between the top layer and the bottom layer, and the intermediate layer having an uneven surface sufficient for a plurality of gaps to form at a contact surface between the sphygmomanometer cuff and an arm of a user, and wherein the surface areas of all three layers are substantially identical so that their edges overlap each other and be adhered to each other;
    a retaining plate, attached to an outer surface of the top layer of the air bag; and
    an air tube, extending through the retaining plate and connecting with the sealed cavity of the air bag.

7. The wearable sphygmomanometer of claim 6, wherein the intermediate layer is attached to an inner surface of the bottom layer or to an inner surface of the top layer.

8. The wearable sphygmomanometer of claim 6, wherein a bottom surface of the retaining plate is arcuate, and the bottom surface recesses toward a top surface of the retaining plate.

9. The wearable sphygmomanometer of claim 6, wherein a plurality of first protrusions are formed intermittently on a bottom of the retaining plate, so that the plurality of first protrusions intermittently contact the outer surface of the top layer of the air bag.

10. The sphygmomanometer of claim 6, wherein a plurality of second protrusions are formed intermittently on a bottom of the retaining plate and surround the air tube, and the plurality of second protrusions intermittently contact the outer surface of the top layer of the air bag.

11. A method for using a wearable sphygmomanometer, comprising:
    providing a wearable sphygmomanometer, the wearable sphygmomanometer comprising a sphygmomanometer main body and a sphygmomanometer cuff, the sphygmomanometer cuff comprising a cuff body for wrapping around a predetermined portion of a body, the cuff body comprising:
    an air bag, comprising a top layer, a bottom layer, and an intermediate layer disposed between and spacing apart the top layer and the bottom layer, wherein a sealed cavity is defined between the top layer and the bottom layer, and the intermediate layer has an uneven surface sufficient for a plurality of gaps to form at a contact surface between the sphygmomanometer cuff and an arm of a user, and wherein the surface areas of all three layers are substantially identical so that their edges overlap each other and be adhered to each other;
    a retaining plate, attached to an outer surface of the top layer of the air bag; and an air tube, extending through the retaining plate and connecting with the seal cavity of the air bag; and
    wrapping the sphygmomanometer cuff around the predetermined portion of the body,
    wherein when a user wears the wearable sphygmomanometer, the air bag of the sphygmomanometer cuff abuts against the predetermined portion of the body, the top layer and the bottom layer of the air bag are disposed adjacent to each other, and the rough surface of the intermediate layer of the air bag allows a plurality of gaps to form at a contact area between the cuff body and the predetermined portion of the body, so as to improve skin respiration,
    when the wearable sphygmomanometer performs a measurement of blood pressure, external air flows through the air tube to inflate the sealed cavity of the air bag, and the rough surface of the intermediate layer prevents the top layer and the bottom layer from adhering to each other, so as to expedite inflation of the sealed cavity of the air bag, and
    when the wearable sphygmomanometer completes the measurement, air in the sealed cavity of the air bag is released through the air tube, and the rough surface of the intermediate layer prevents the top layer and the bottom layer from adhering to each other, so as to expedite deflation of the sealed cavity of the air bag.

12. The method of claim 11, wherein a bottom surface of the retaining plate is arcuate, the bottom surface recesses toward a top surf ace of the retaining plate, when the user wears the wearable sphygmomanometer, the retaining plate abuts against the air bag, the top layer and the bottom layer of the air bag are disposed adjacent to each other, and an air channel is formed at the arcuate bottom surface of the retaining plate between the top layer and the bottom layer and is connected with the air tube, so as to facilitate inflation and deflation of the air bag.

13. The method of claim 11, wherein a plurality of first protrusions are formed intermittently on a bottom of the retaining plate, so that the plurality of first protrusions intermittently contact the outer surface of the top layer of the air bag, when the wearable sphygmomanometer performs the measurement of blood pressure, the retaining plate abuts against the air bag, the top layer of the air bag abuts against the plurality of first protrusions to form a plurality of intermittent air passages in the sealed cavity, and the air passages are connected with the air tube, so as to facilitate inflation and deflation of the air bag.

14. The method of claim 11, wherein a plurality of second protrusions are formed intermittently on a bottom of the retaining plate and surround the air tube, so that the plurality of second protrusions intermittently contact the outer surface of the top layer of the air bag, when the wearable sphygmomanometer performs the measurement of blood pressure, the retaining plate abuts against the air bag, the top layer of the air bag abuts against the plurality of second protrusions to form a plurality of intermittent air passages in the sealed cavity, and the air passages are connected with the air tube, so as to facilitate inflation and deflation of the air bag.

* * * * *